United States Patent [19]

Frassica et al.

[11] Patent Number: 5,419,310
[45] Date of Patent: May 30, 1995

[54] PARTIALLY INFLATED PROTECTIVE ENDOSCOPE SHEATH

[75] Inventors: James J. Frassica, Chelmsford; Robert E. Ailinger, Norwood; Mary L. DeBaryshe, Bedford; Robert Herrington, Holland; James S. Surette, North Reading; Alan I. West, Hopkinton, all of Mass.

[73] Assignee: Vision Sciences, Inc., Natick, Mass.

[21] Appl. No.: 970,719

[22] Filed: Nov. 3, 1992

[51] Int. Cl.⁶ .............................................. A61B 1/00
[52] U.S. Cl. ....................................................... 128/4
[58] Field of Search .................. 128/4, 6; 604/96, 103, 604/163, 263

[56] References Cited

U.S. PATENT DOCUMENTS

| | | |
|---|---|---|
| 2,548,602 | 4/1951 | Greenburg . |
| 2,797,683 | 7/1957 | Aiken . |
| 2,922,415 | 1/1960 | Campagna . |
| 2,958,364 | 11/1960 | Thompson . |
| 3,144,020 | 8/1964 | Zingale . |
| 3,162,190 | 12/1964 | Del Gizzo . |
| 3,426,749 | 2/1969 | Jephcott . |
| 3,739,770 | 6/1973 | Mori . |
| 3,750,875 | 8/1973 | Juster . |
| 3,794,091 | 2/1974 | Ersek et al. . |
| 3,797,734 | 3/1974 | Fleury et al. . |
| 3,809,072 | 5/1974 | Ersek et al. . |
| 3,831,587 | 8/1974 | Boyd . |
| 3,861,395 | 1/1975 | Taniguchi . |
| 3,866,601 | 2/1975 | Russell . |
| 3,956,011 | 5/1976 | Carleton . |
| 3,960,143 | 6/1976 | Terada . |
| 3,971,385 | 7/1976 | Corbett ............................. 604/96 X |
| 3,980,078 | 9/1976 | Tominaga . |
| 4,024,858 | 5/1977 | Chikama . |
| 4,065,816 | 1/1978 | Sawyer . |
| 4,076,018 | 2/1978 | Heckele . |
| 4,085,742 | 4/1978 | Okada . |
| 4,132,227 | 1/1979 | Ibe . |
| 4,141,364 | 2/1979 | Schultze . |
| 4,182,478 | 1/1980 | Etes . |
| 4,201,199 | 5/1980 | Smith . |
| 4,230,115 | 10/1980 | Walz, Jr. et al. . |
| 4,248,214 | 2/1981 | Hannah et al. . |
| 4,254,762 | 3/1981 | Yoon . |
| 4,256,102 | 3/1981 | Monaco . |
| 4,277,168 | 7/1981 | Oku . |
| 4,299,244 | 11/1981 | Hirai . |
| 4,327,735 | 5/1982 | Hampson . |
| 4,329,995 | 5/1982 | Anthracite . |
| 4,356,610 | 11/1982 | Hon et al. . |
| 4,406,656 | 9/1983 | Hattler et al. . |
| 4,461,282 | 7/1984 | Ouchi et al. . |

(List continued on next page.)

FOREIGN PATENT DOCUMENTS

| | | |
|---|---|---|
| 0055393 | 11/1981 | European Pat. Off. . |
| 0104618 | 9/1983 | European Pat. Off. . |
| 0184399 | 11/1985 | European Pat. Off. . |
| 0184778 | 12/1985 | European Pat. Off. . |
| 0184778B1 | 12/1985 | European Pat. Off. . |
| 0338567 | 4/1989 | European Pat. Off. . |
| 0341719 | 11/1989 | European Pat. Off. . |
| 2150595 | 10/1972 | Germany . |

(List continued on next page.)

OTHER PUBLICATIONS

Mark, James E.; Odian, George; "Polymer Chemistry"; ACS Short Courses; Feb. 1992; p. 104.

*Primary Examiner*—Richard J. Apley
*Assistant Examiner*—Beverly A. Meindl
*Attorney, Agent, or Firm*—Seed and Berry

[57] ABSTRACT

A partially elastic protective sheath surrounding the insertion tube of an endoscope. The sheath is partially inflated while being installed on the endoscope and remains partially inflated during endoscopy. The sheath has an end cap with a gasket shaped to provide a seal around the insertion tube during installation and endoscopy. The sheath is provided with a window near its distal end positioned in front of the viewing window of the endoscope. The sheath may have one or more channels extending along its length to accommodate one or more biopsy or fluid tubes of the endoscope. The sheath may be used with either end-viewing endoscopes or side-viewing endoscopes.

4 Claims, 3 Drawing Sheets

U.S. PATENT DOCUMENTS

| | | |
|---|---|---|
| 4,519,385 | 5/1985 | Atkinson et al. . |
| 4,524,802 | 6/1985 | Lawrence et al. . |
| 4,537,209 | 8/1985 | Sasa . |
| 4,550,440 | 10/1985 | Rico . |
| 4,592,341 | 6/1986 | Omagari et al. . |
| 4,593,699 | 6/1986 | Poncy et al. . |
| 4,606,330 | 8/1986 | Bonnet . |
| 4,616,631 | 10/1986 | Takahashi . |
| 4,620,527 | 11/1986 | Adams, Jr. . |
| 4,633,882 | 1/1987 | Matsuo et al. . |
| 4,646,722 | 3/1987 | Silverstein et al. . |
| 4,669,172 | 6/1987 | Petruzzi . |
| 4,676,228 | 6/1987 | Krasner et al. . |
| 4,676,229 | 6/1987 | Krasnicki et al. . |
| 4,681,093 | 7/1987 | Ono et al. .............................. 128/6 |
| 4,691,738 | 9/1987 | McCune . |
| 4,721,097 | 1/1988 | D'Amelio . |
| 4,726,355 | 2/1988 | Okada . |
| 4,741,326 | 5/1988 | Sidall et al. . |
| 4,742,816 | 5/1988 | Suzuki et al. . |
| 4,742,829 | 5/1988 | Law et al. . |
| 4,754,877 | 7/1988 | Johansson et al. . |
| 4,763,662 | 8/1988 | Yokoi . |
| 4,772,275 | 9/1988 | Erlich . |
| 4,773,395 | 9/1988 | Suzuki et al. . |
| 4,784,158 | 11/1988 | Okimoto . |
| 4,787,753 | 11/1988 | Barnhart . |
| 4,794,911 | 1/1989 | Okada . |
| 4,800,870 | 1/1989 | Reid, Jr. . |
| 4,807,593 | 2/1989 | Ito . |
| 4,815,470 | 3/1989 | Curtis et al. . |
| 4,825,850 | 5/1989 | Opie et al. . |
| 4,852,551 | 8/1989 | Opie et al. . |
| 4,854,302 | 8/1989 | Allred, III . |
| 4,869,238 | 9/1989 | Opie et al. . |
| 4,886,049 | 12/1989 | Darras ...................... 128/4 |
| 4,907,395 | 3/1990 | Opie et al. . |
| 4,928,669 | 5/1990 | Sullivan . |
| 4,947,827 | 8/1990 | Opie et al. . |
| 4,991,565 | 2/1991 | Takahashi et al. ...................... 128/4 |
| 4,997,084 | 3/1991 | Opie et al. . |
| 5,019,042 | 5/1991 | Sahota ............... 604/96 X |
| 5,025,778 | 6/1991 | Silverstein et al. . |
| 5,050,585 | 9/1991 | Takahashi ................................ 128/4 |
| 5,078,681 | 1/1992 | Kawashima ................ 604/96 X |
| 5,159,919 | 11/1992 | Chikama ................................ 128/4 |
| 5,159,920 | 11/1992 | Condon et al. ...................... 128/4 X |
| 5,201,908 | 4/1993 | Jones ........................ 128/4 |
| 5,217,001 | 6/1993 | Nakao et al. .............................. 128/4 |
| 5,237,984 | 8/1993 | Williams, III et al. .................. 128/4 |

FOREIGN PATENT DOCUMENTS

| | | |
|---|---|---|
| 3508833 | 9/1986 | Germany ................. 128/4 |
| 775476 | 2/1955 | United Kingdom . |
| 1405025 | 2/1973 | United Kingdom . |
| 2138687 | 4/1984 | United Kingdom . |
| WO89/00832 | 7/1988 | WIPO . |
| WO91/14391 | 3/1991 | WIPO . |

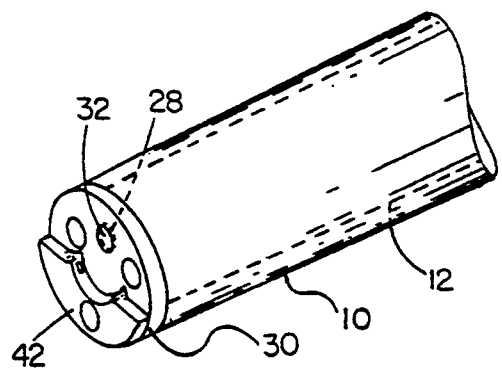
FIG. 4
FIG. 5
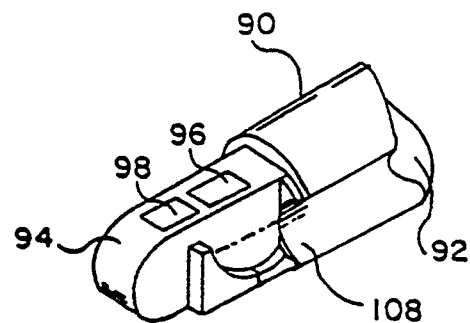
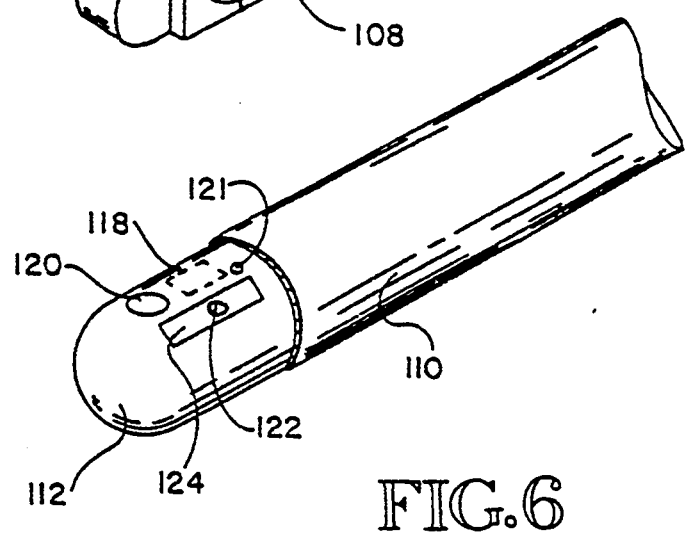
FIG. 6

PARTIALLY INFLATED PROTECTIVE ENDOSCOPE SHEATH

TECHNICAL FIELD

This invention relates to endoscopy, and more particularly, to a device for inexpensively isolating an endoscope from viruses and bacteria.

BACKGROUND OF THE INVENTION

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum, colonoscopes for examining the colon, angioscopes for examining blood vessels, bronchoscopes for examining the bronchi, laparoscopes for examining the peritoneal cavity, and arthroscopes for examining joint spaces. The discussion which follows will apply to all of these types of endoscopes. Instruments to examine the rectum and sigmoid colon, known as flexible sigmoidoscopes, are good examples of the usefulness of this technology. These devices are expensive, used in a contaminated environment for a procedure which is brief (5-10 minutes) and where problems of cleaning time and contamination are important factors. There has been a large increase in the use of the "flexible sigmoidoscope" for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five to ten sigmoidoscope examinations each hour. One significant problem with making such examinations quick and inexpensive is the time necessary for adequately cleaning the device.

Although endoscopes can be cleaned in about two to four minutes, this relatively cursory cleaning may not be adequate for complete disinfection or sterilization. Even a more complete cleaning requiring on the order of eight to ten minutes may not allow adequate cleaning, particularly in view of the increasing problems with contagious viruses. Even with the use of chemicals such as glutaraldehyde, adequate cleanliness may not be possible.

While the external surfaces of endoscopes can often be adequately cleaned, endoscopes typically have air, water, biopsy and suction channels extending along their lengths which come into contact with body tissues or fluids. It is extremely difficult to adequately clean these channels even when skilled health practitioners spend a great deal of time on the cleaning procedure.

Even if endoscopes can be adequately cleaned in eight to ten minutes, the cleaning still prevents endoscopy examinations from being relatively inexpensive. While a physician may spend five to ten minutes performing the endoscopy, he or she will generally waste a great deal of time waiting for the endoscope to be cleaned before he or she can conduct another endoscopy. A partial solution to the "idle time" problem is to purchase multiple instruments so one can be used as the others are being cleaned. However, the expense of having duplicate endoscopes of each type makes this solution impractical especially for physicians' offices and smaller clinics.

Not only must the idle time of the physician be added to the cost of endoscopic examinations, but the time spent by a nurse or other hospital personnel in the cleaning as well as the cost of disinfecting chemicals must also be added to the cost of the examination. Although washing machines are available to clean endoscopes, these machines are expensive and not significantly faster than washing by hand. As a result, with conventional endoscopic procedures, both the physician and the relatively expensive endoscope have a downtime approaching fifty percent.

Another problem with cleaning endoscopes by hand or with a washing machine is that the chemicals used are toxic and potentially injurious to the staff who use them, and the environment into which they are discharged. To use some of these chemicals safely, such as glutaraldehyde, requires a dedicated ventilated hood, which uses up space and is expensive to install and operate. The chemicals are also potentially toxic to the patient in that if residue remains after cleaning and rinsing the instrument, the patient could have a reaction to the chemicals. A limitation to this approach is that some types of chemicals may damage the outer surfaces of endoscopes after a number of washings.

In short, conventional endoscope cleaning techniques greatly increase the cost of endoscopic procedures. Furthermore, while the risk of contamination using endoscopes is often far less than the risk of alternative procedures, such as surgery, there is nevertheless a risk that endoscopes are not adequately cleaned to prevent the risk of transmission of infectious diseases from one patient to the next.

In the health care field, the problems of contaminated instruments transmitting disease from one patient to the next have generally been solved by making such instruments disposable. However, this has not been thought possible in the field of endoscopy because endoscopes are very sophisticated, and hence, expensive instruments. Moreover, it has not been thought possible to isolate the endoscope from the patient or the external environment because the endoscope itself has channels inside it that are used as a conduit for body fluids and tissues, such as, for example, in taking biopsies. The only method currently available to actually sterilize an endoscope is to use gas sterilization with ethylene oxide (ETO) gas. However, there are several significant disadvantages in using this procedure. The procedure is very slow; it takes 24 hours, during which the endoscope cannot be used. Also, the gas affects the plastic of the endoscope and may limit the life span of the instrument. The gas is toxic, and, therefore, great care must be taken to ensure that no residue remains that might cause patient irritation during contact with the endoscope. Finally, if the instrument is not thoroughly cleaned of all tissue, mucous, blood and stool, a biofilm is formed which is impenetrable, and easily killed microbes have been cultured from such endoscopes after ETO "sterilization."

U.S. Pat. No. 4,646,722, which is incorporated by reference herein, teaches the use of a disposable elastomeric sheath which is installed by inflation. The inside diameter of the sheath is undersized to the outside diameter of the endoscope such that the sheath fits the endoscope snugly upon deflation. One of the problems encountered with this approach is the possibility of over inflation of the sheath. U.S. Pat. No. 4,907,395 describes the use of an elongated bag to package the sheath and also prevent such overexpansion by acting as a restraint; the sheath expands until it contacts the wall of the bag.

U.S. Pat. No. 4,991,564 addresses the issue of over inflation of the elastomeric sheath by incorporating a pressure relief valve in the inflation means. Such an approach overcomplicates the installation or removal of the sheath, especially since higher pressures may be initially required when beginning to inflate the sheath. Additionally, there may be times when the user desires to adjust the sheath, such as if the distal window of the sheath is not properly aligned with the viewing optics of the endoscope. Under these circumstances, it would be inconvenient to have to replace the sheathed endoscope back into the bag to make such adjustment. Another problem with the use of an elastomeric sheath, such as latex, is that longitudinal as well as radial expansion occurs upon inflation, and this can leave a loose, "baggy" distal end as the sheath deflates at the proximal end first. This is a problem as a tight fit is desirable for the entire length of the endoscope for manipulation. U.S. Pat. No. 4,991,564 addresses this problem by the use of a tapered sheath cover to reduce the chance of the sheath bunching up at the distal end during installation. Still another problem with the use of elastomer materials is the possibility of pinholes and tears resulting in a compromise of the barrier properties of the sheath.

The need to inflate the sheath so that it expands to contact the wall of the elongated bag, as taught in U.S. Pat. No. 4,907,395, requires a good seal at the proximal end of the sheath where the endoscope enters. U.S. Pat. No. 4,991,565 addresses this problem by use of a gasket-type seal that is free to move radially, thus allowing complete sealing around the endoscope as it is bent and moves during installation. One of the problems with this approach is pressure build-up within the sheath as the endoscope is advanced towards the distal end of the sheath, further compressing the gas. Such increased pressure will cause resistance as the endoscope is advanced, and may prevent proper seating of the distal window of the sheath against the endoscope optics. In this regard, it is important for the proximal seal between the endoscope and sheath to leak in a controlled manner so as to prevent this pressure build-up.

The placement of a tightly fitting sheath onto an endoscope can detrimentally restrict the movement and flexibility of the endoscope. Traditional endoscopes have an insertion tube constructed of a vinyl or urethane covered spring to which is coupled the articulating section comprised of metal vertebrae loosely covered with a rubber material. Such a construction gives the required axial and torsional rigidity for most of the length of the endoscope along with a more flexible articulating section which can be moved with little applied force in a relatively tight bending radius. The placement of a tight fitting sheath surrounding the endoscope, although it is needed for the length of the insertion tube, can result in poor mobility at the articulating section.

One might consider the use of a loose bag as a sheath material since one would not have to inflate it for installation, and it would not restrict the movement of the tubes contained within. Ersek in U.S. Pat. Nos. 3,794,091 and 3,809,072 describes such a design. While this would allow the tubes to more freely move during articulation of the endoscope, the bagginess of such a sheath would create discomfort for the patient during insertion of the endoscope, and it would not allow the physician to grip the endoscope tube with sufficient purchase during manipulation.

SUMMARY OF THE INVENTION

It is an object of this invention to provide a protective sheath for an endoscope which can be rapidly and simply installed and removed.

It is another object of this invention to provide a protective sheath for an endoscope which is tough and not easily torn, and therefore retains its barrier properties against microbes.

It is still another object of this invention to provide a protective sheath for an endoscope which is limited in its expansion such that inflation does not result in the sheath expanding longitudinally to an appreciable degree.

It is another object of the invention to provide a protective sheath which fits the outside of an endoscope in a snug manner, thus resulting in an endoscope and sheath assembly that has the same "feel" and torque characteristics as conventional endoscopes.

Finally, it is an object of the invention to provide a protective sheath for an endoscope which is partially inflated by a fluid such as air in order to achieve unrestrained movement of the endoscope during use.

These and other objects of the invention are provided for in the design of a partially elastic sheath which inflates in a controlled manner i.e., expands very little longitudinally, but enough radially for installation of the sheath over the endoscope. The sheath may remain partially inflated while the endoscope is being used. Partial inflation of the sheath allows for optimum patient comfort as it offers a smooth surface and a low profile to the patient as well as good manual manipulation for the physician as it is not so inflated as to prevent effective torsional control.

BRIEF DESCRIPTION OF THE DRAWINGS

FIG. 4 is an expanded isometric view showing the distal end of the endoscope and protective sheath.

FIG. 5 is an isometric view of the distal end of a side-view endoscope.

FIG. 6 is an isometric view of the protective sheath adapted for a side-view endoscope.

DETAILED DESCRIPTION OF THE INVENTION

Figure 1:
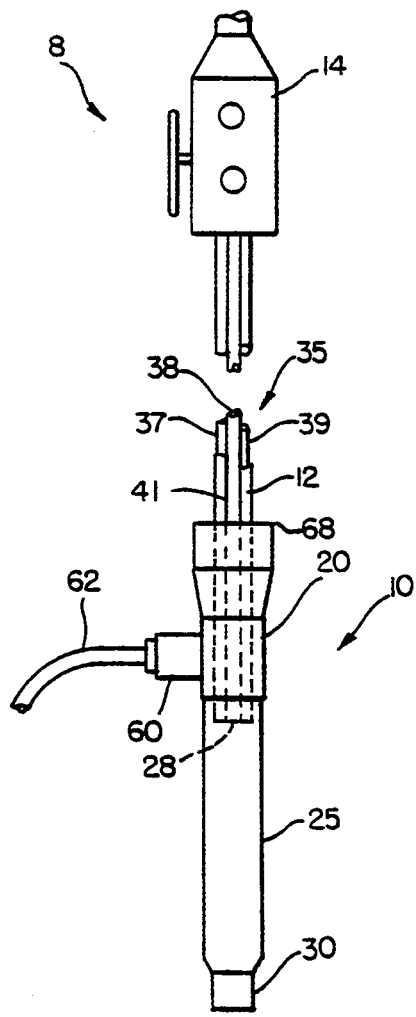
FIG. 1 is a side view of an endoscope being inserted into the inventive protective sheath.

FIG. 1 shows an endoscope 8 having insertion tube 12 extending from a headpiece 14 and partially inserted into an inventive endoscope sheath 10. The sheath 10 includes an inflation section 20, an expansion section 25, and a distal end cap 30. The sheath expansion section 25 is made from a resilient material, such as polyvinylchloride or polyurethane, with a wall thickness of about 0.01 inch, which is sufficiently elastic for partial radial expansion, but which resists longitudinal expansion. Furthermore, the thickness and elastic properties of the sheath expansion section 25 are preferably selected in a known manner to control the expansion of the expansion section 25. More specifically, the expansion section 25 preferably expands as a linear function of its internal pressure until it is spaced a predetermined distance from the endoscope insertion tube 12. Thereafter, the expansion section 25 preferably does not expand significantly in response to further increase in its internal pressure. In other words, the elastic limit of the expansion section 25 is selected in a known manner to be a predetermined dimension greater than the diameter of the insertion tube 12. This "controlled elasticity" makes it unnecessary to precisely limit the inflation pressure or otherwise provide means to restrict expansion of the expansion section 25.

The sheath inflation section 20 is equipped with an inflation nozzle 60 which allows a fluid, usually air, to be forced into the sheath 10. The inflation nozzle 60 communicates with an inflation tube 62, which is connected to an inflation pump (not shown). The inflation pump forces approximately 3 psi of air through the inflation tube 62 and the inflation nozzle 60 and into the sheath 10. This air pressure expands the sheath 10 slightly to allow the endoscope insertion tube 12 to be easily inserted completely into the sheath 10. In contrast to prior art protection systems, sheath 10 preferably remains partially inflated while the endoscopy is performed.

The endoscope insertion tube 12 will normally include structure for illuminating tissues and conveying an image of the tissues viewed to the endoscope headpiece 14. The distal end of the insertion tube 12 is provided with a transparent lens 28 that allows the image to be received by the endoscope. It is of the utmost importance that the insertion tube 12 be freely maneuverable so that the desired tissues can be viewed.

Figure 2:
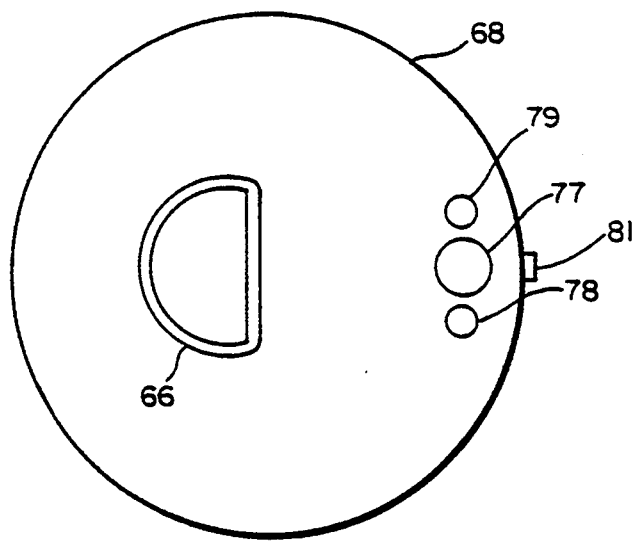
FIG. 2 is an end view of the proximal fitting of the endoscope sheath.
Figure 3:
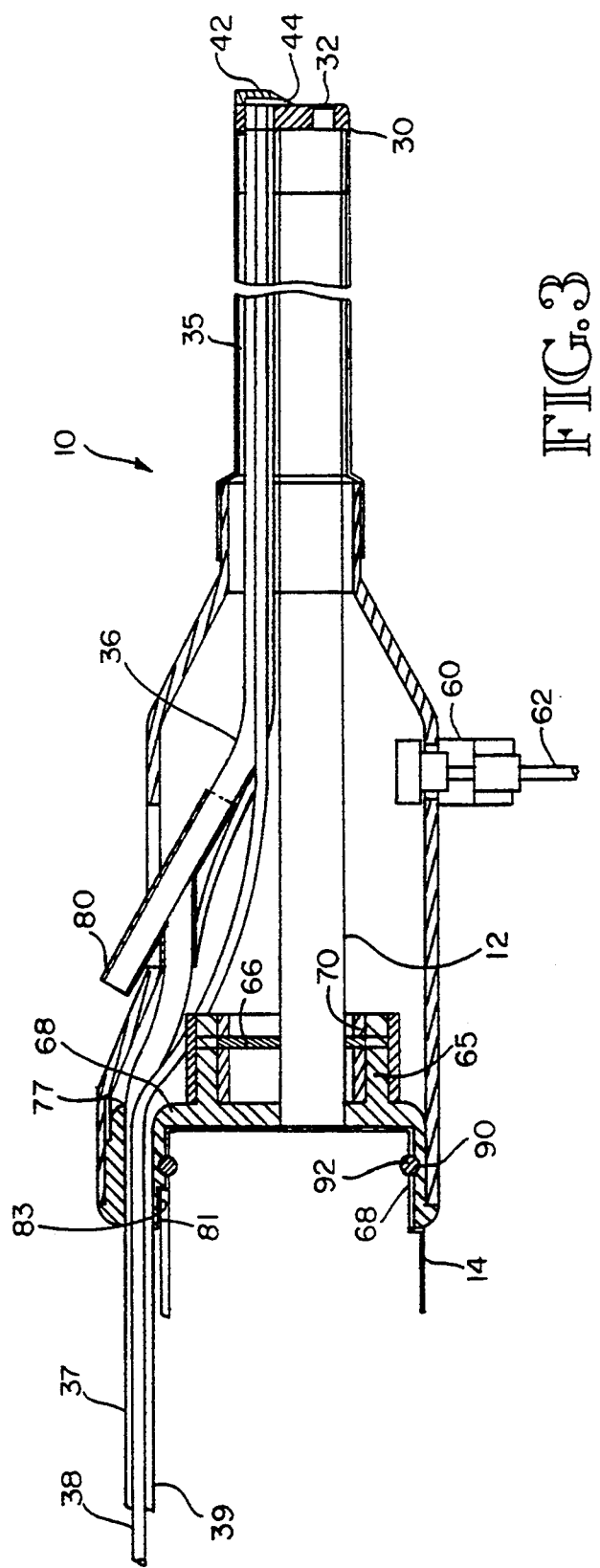
FIG. 3 is a longitudinal sectional view of the endoscope sheath and the endoscope, including the insertion tube.

With further reference to FIGS. 2 and 3, although not required for imaging internal body tissues, endoscopes will also usually have a system of channels 35 extending from the headpiece 14 to the distal end of the insertion tube 12 for performing a variety of functions. One of these tubes is a wash channel 38 by which pressurized water can be injected through a nozzle at the distal end of the insertion tube 12 onto the endoscope viewing lens 28 in order to clean the lens of body tissues and fluids. Another channel 39 is used to instill air or $CO_2$ gas to distend the hollow organ and permit visual inspection. A plate 42 is mounted on the end of the end cap 30. The plate 42 directs water from the wash channel 38 to a channel 44 formed as a groove in plate 42. Plate 42 thus changes the flow of water to a direction 90° to the original direction of channel 38. Water from the wash channel 38 is thus sprayed onto the window 32 to clean it. A similar channel (not shown) extends from the gas channel 39 toward the outer face of the window 32 to blow debris away from the window 32. A suction tube 37 extending the length of the endoscope insertion tube 12 may also be used to extract fluids or to inject fluids into the body. Finally, various biopsy and other devices, both diagnostic and therapeutic, may be inserted through biopsy channel 36 to perform a specific function at the distal end of the insertion tube 12 (FIG. 3). Although FIG. 1 shows the channel system 35 to be within an externally accessible groove 41 formed in the insertion tube 12, it may be more practical to position the channel system 35 outside of the insertion tube 12 as in FIG. 3. Positioning the channel system 35 outside of the insertion tube 12 allows the channel system 35 to more easily be cleaned or disposed of separately from the insertion tube 12.

To allow the sheath 10 to be inflated to receive the insertion tube 12, a sealing means is required to prevent excessive leakage from the proximal end of the sheath 10. The sealing means includes a proximal end cap 68 located at the proximal end of the sheath 10. FIG. 2 shows an end view of the proximal end cap 68, while FIG. 3 shows a cross section of the headpiece 14 of the endoscope 8 abutting the end cap 68 with the insertion tube 12 of the endoscope 8 extending into the sheath 10. The proximal end cap 68 includes a distally projecting spacer 65 on which a proximal gasket 66 is mounted. The proximal gasket 66 is made from an elastic material, such as rubber, which allows the sheath 10 to remain inflated while the endoscope 8 is being used. Proximal gasket 66 should be sized and shaped so as to fit snugly on the insertion tube 12 when the insertion tube 12 is inserted through the center of the gasket 66 to prevent excessive air leakage, yet not so tightly as to prevent all leakage. Some leakage is necessary so that the pressure inside the sheath does not become excessive while the insertion tube 12 is being inserted and is displacing the air within the sheath 10. Excessive air pressure within the sheath 10 would prevent the insertion tube 12 from extending to the distal end of the sheath 10, thereby preventing the sheath window 32 from fitting properly over the endoscope viewing lens 28. A washer 70 may be employed to help retain the proximal gasket 66 to the proximal end cap 68 (FIG. 3). The spacer 65 spaces the gasket 66 away from the proximal end cap 68 so that the gasket 66 can deflect in the distal direction when the insertion tube 12 is inserted and in the proximal direction when the insertion tube 12 is removed from the sheath. A groove 90 is preferably formed in the interior surface of the proximal end cap 68. The groove 90 receives a snap ring 92 surrounding the endoscope headpiece 14 to lock the headpiece 14 in position within the end cap 68. For example, as shown in FIG. 3, the headpiece 14 may include an outwardly projecting ridge 81 that fits into a slot 83 formed in the end cap 68. The headpiece 14 is preferably shaped to key into a similarly shaped portion of the proximal end cap to prevent the endoscope from rotating within the sheath.

FIG. 2 shows the proximal end cap 68 designed for a D-shaped endoscope insertion tube 12 having a channel system 35 located on the outside of the insertion tube 12. In this embodiment, the proximal end cap 68 includes a suction port 77 which receives the suction channel 37; a water port 78 which receives the wash channel 38; and a gas port 79 which receives the air channel 39. The proximal end cap 68 may be designed to include a port for the biopsy channel 36. However, preferably the sheath 10 includes a separate biopsy port 80 as shown in FIG. 3. The proximal end cap 68 and proximal gasket 66 allow the endoscope sheath 10 to be partially inflated for installation of the insertion tube 12 within the sheath 10. When fully installed, the proximal gasket 66 allows the sheath 10 to remain partially inflated while the endoscope 8 is being used.

When the endoscope insertion tube 12 is fully in place within the sheath 10, the pressure may be reduced to approximately 3 psi for use during an endoscopic procedure. The reduced pressure partially deflates the sheath 10 to allow the insertion tube 12 and sheath 10 to more easily be inserted into the patient. It should be recognized that other pressures may be used to accomplish the inflation depending upon the expandability of the sheath 10. The pressure should be enough to provide the desired cushioning, but not too much so as to inhibit maneuverability of the insertion tube 12 and channel system 35.

In contrast to that of the prior art, the sheath 10 remains partially inflated while the endoscopy is performed. The partially inflated sheath allows complete movement of the distal end of the endoscope, as the insertion tube 12 and channel tube system 35 are free to move within the sheath 10 during articulation. In an alternate embodiment, the walls of the distal end of the sheath expansion section 25 may be made thinner than the walls of the remainder of the expansion section 25 so that the expansion section 25 expands more at its distal end. This allows the distal end of the insertion tube 12 to move more freely within the sheath 10. In either embodiment the positive pressure inside the sheath 10 provided through the inflation tube 62 ensures the maintenance of the sheath's barrier properties as microbes and other bodily materials will not be able to enter a break in the sheath and contaminate the endoscope 8. The partially inflated sheath 10 should provide more comfort for the patient as it may act as a pneumatic bumper, cushioning the body during insertion and withdrawal.

After an endoscopy has been performed, the sheath 10 may be removed from the insertion tube 12, leaving the insertion tube sterilized (if it was sterilized beforehand) without the need for expensive and time-consuming washing. It will also be apparent that if the insertion tube 12 was not sterile before the protective sheath 10 was applied, the protective sheath also isolates the patient from the nonsterile insertion tube. When the sheath and channel systems are removed and disposed of after the procedure, the insertion tube should remain clean. A backup assurance occurs when a new sterile sheath is installed prior to the next patient's examination to protect that patient in case some contamination of the insertion tube 12 did occur during the prior procedure.

As shown in FIG. 4, the distal end of the protective sheath 10 includes a distal end cap 30 having a viewing window 32 mounted thereon. When the insertion tube 12 is fully in place within the sheath 10, the distal end cap 30 fits tightly on the distal end of the insertion tube. The sheath window 32 is positioned above the endoscope viewing lens 28 to allow the internal environment of the patient to be viewed. While being used, the sheath window 32 tends to build up bodily tissues and fluids. As explained earlier, a plate 42 having an internal wash channel and an internal gas channel is mounted on the end cap 30 to direct water and gas onto the outer surface of the window 32.

The inventive endoscope sheath may also be used with side-looking endoscopes. As illustrated in FIG. 5, side-viewing endoscope 90 includes a endoscope insertion tube 92 terminating in a cap 94 having a viewing window 96 and a light source 98 on an axial face. As is well known in the art, light is emitted from the light source 98 to allow tissues to be viewed through the window 96. The endoscope 90 may include a longitudinal groove 108 extending along the length of the insertion tube 12, the longitudinal groove 108 being adapted to receive a channel system similar to channel system 35 shown in FIGS. 1, 3 and 4. Instead of having groove 108, endoscope 90 may be modified to position the channel system outside of the insertion tube 12, similar to the system shown in FIG. 3.

The protective sheath 110 for side-viewing endoscopes is illustrated in FIG. 6, with the sheath installed on the endoscope. The sheath 110 includes an end cap 112 of relatively rigid material mounted at the end of a resilient cylindrical tube. The end cap 112 includes a pair of transparent windows 118, 120 positioned over the viewing window 96 and the light source 98, respectively, of the endoscope (FIG. 5). Light emitted by the endoscope through window 98 shines through window 120 to illuminate internal body tissues. These tissues are then viewed through the window 118 of the end cap 112 and through window 96 of the endoscope. A wash port 121 is connected to a wash tube in a manner similar to wash port 42 and wash tube 38 of the embodiment of FIG. 4 to maintain window 118 free of substances that would otherwise obscure the view of the internal environment of the patient.

As with end-view endoscope of FIGS. 1-2, the sheath 110 is partially inflated to receive the endoscope 90 and remains partially inflated while the endoscopy is performed. The inflation and sealing means is the same for both end-view and side-view endoscopes. This allows the same cushioning, free movement, and increased protection as discussed above.

The invention allows endoscopes to be used in a manner that prevents patient contamination without time-consuming, expensive and unsatisfactory washing. Since several sheath configurations are possible, all fitting over the same core endoscope, this system allows the endoscopist to use one core endoscope and yet have a family of different endoscopes as various specific sheaths are used. Furthermore, since multiple channel configurations can be considered with a sheath designed for a specific purpose, new technologies may be possible via the endoscope, such as multiple electrical wires to activate an ultrasound device or hydraulic channels to activate a hydraulic device.

While the invention has been described with reference to specific embodiments, it should be apparent that numerous modifications may be made by those skilled in the art without departing from the scope of the invention.

We claim:

1. For an endoscope having an elongated insertion tube with distal and proximal ends, a protective sheath comprising:

a resilient, elongated sheath tube having a controlled elasticity, said sheath tube having distal and proximal ends and adapted to receive the endoscope insertion tube; said sheath tube having side walls that are thinner at the distal end of said sheath tube than at its proximal end so as to allow increased expansion of said sheath tube at its distal end compared to its proximal end;

inflation means for injection of a fluid into the sheath tube, thereby partially expanding the sheath tube to form a layer of the fluid, thereby spacing the sheath tube away from the insertion tube; and sealing means for retaining fluid in the sheath tube, for retaining the sheath tube in an expanded state, and for retaining space between the sheath tube and the insertion tube while the endoscope is being used for an endoscopic procedure.

2. A method of isolating an endoscope during an endoscopy, said endoscope having an elongated insertion tube with distal and proximal ends, said method comprising:

inserting the insertion tube into a resilient, elongated sheath so that the distal end of the insertion tube becomes adjacent the distal end of the sheath;

injecting fluid into the sheath, thereby expanding the sheath and forming a space between the sheath and the insertion tube, the space being filled with the fluid; and retaining the fluid in the space between the sheath and the insertion tube while the endoscope is used during the endoscopy, thereby keeping the sheath expanded during the endoscopy.

3. The method of claim 2, further including the step of varying the elastic properties of the sheath along its length so that the sheath expands to a greater degree toward its distal end.

4. The method of claim 2, further including the step of injecting the fluid into the sheath tube while the insertion tube is being inserted into the sheath tube.

* * * * *